US009624153B2

(12) United States Patent
Becker et al.

(10) Patent No.: US 9,624,153 B2
(45) Date of Patent: Apr. 18, 2017

(54) TWO-STAGE HYDROFORMYLATION PROCESS WITH CIRCULATING GAS AND SILP TECHNOLOGY

(71) Applicants: Evonik Degussa GmbH, Essen (DE); Marc Becker, Dortmund (DE); Katrin Marie Dyballa, Recklinghausen (DE); Robert Franke, Marl (DE); Dirk Fridag, Haltern am See (DE); Hanna Hahn, Duisburg-Baerl (DE); Marina Lazar, Langenselbold (DE); Markus Priske, Salzburg (AT); Guido Stochniol, Haltern am See (DE)

(72) Inventors: Marc Becker, Dortmund (DE); Katrin Marie Dyballa, Recklinghausen (DE); Robert Franke, Marl (DE); Dirk Fridag, Haltern am See (DE); Hanna Hahn, Duisburg-Baerl (DE); Marina Lazar, Langenselbold (DE); Markus Priske, Salzburg (AT); Guido Stochniol, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/103,842

(22) PCT Filed: Dec. 10, 2014

(86) PCT No.: PCT/EP2014/077110
§ 371 (c)(1),
(2) Date: Jun. 10, 2016

(87) PCT Pub. No.: WO2015/086634
PCT Pub. Date: Jun. 18, 2015

(65) Prior Publication Data
US 2016/0304426 A1 Oct. 20, 2016

(30) Foreign Application Priority Data
Dec. 13, 2013 (DE) .......................... 10 2013 225 883

(51) Int. Cl.
| | | |
|---|---|---|
| C07C 45/50 | (2006.01) |
| B01D 5/00 | (2006.01) |
| B01J 31/00 | (2006.01) |
| B01D 61/38 | (2006.01) |
| B01J 31/02 | (2006.01) |
| B01J 31/18 | (2006.01) |
| C07C 45/78 | (2006.01) |
| B01D 61/36 | (2006.01) |
| B01J 31/24 | (2006.01) |
| C07C 45/79 | (2006.01) |
| C07C 45/82 | (2006.01) |

(Continued)

(52) U.S. Cl.
CPC .............. *C07C 45/50* (2013.01); *B01D 5/006* (2013.01); *B01D 5/0072* (2013.01);
(Continued)

(58) Field of Classification Search
CPC ....... C07C 45/50; C07C 45/786; B01D 5/006; B01D 6/362; B01J 31/0292; B01J 31/1845
(Continued)

(56) References Cited

U.S. PATENT DOCUMENTS

| | | |
|---|---|---|
| 4,593,127 A | 6/1986 | Bunning et al. |
| 6,414,202 B1 | 7/2002 | Baker et al. |

(Continued)

FOREIGN PATENT DOCUMENTS

| | | |
|---|---|---|
| DE | 10128325 A1 | 2/2002 |
| EP | 2280920 B1 | 12/2011 |

(Continued)

OTHER PUBLICATIONS

Riisager et al. Propene and 1-octene hydroformylation with silica-supported, ionic liquid-phase (SILP) Rh-phosphine catalyts in continuous fixed-bed mode. Catalyst Letters, 2003, vol. 90 (3-4), 149-153.*
International Search Report and Written Opinion, PCT/EP2014/077110, Jun. 18, 2015.

*Primary Examiner* — Sikarl Witherspoon
(74) *Attorney, Agent, or Firm* — Michael Best & Friedrich LLP

(57) ABSTRACT

The invention relates to processes for preparing aldehydes by hydroformylation of alkenes, in which an alkene-containing feed mixture is subjected to a primary hydroformylation with synthesis gas in the presence of a homogeneous catalyst system, the primary hydroformylation being effected in a primary reaction zone from which a cycle gas containing at least some of the products and unconverted reactants of the primary hydroformylation are drawn off continuously and partly condensed, with recycling of uncondensed components of the cycle gas into the primary reaction zone, and with distillative separation of condensed components of the cycle gas in an aldehyde removal stage to give an aldehyde-rich mixture and a low-aldehyde mixture. The problem that it addresses is that of developing the process such that it achieves high conversions and affords aldehyde in good product quality even in the case of a deteriorating raw material position. More particularly, a solution is to be found for making legacy oxo process plants capable of utilizing lower-value raw material sources. This problem is solved by separating the low-aldehyde mixture into a retentate and a permeate by means of a membrane separation unit in such a way that alkenes present in the low-aldehyde mixture become enriched in the permeate, while alkanes present in the low-aldehyde mixture become enriched in the retentate. The alkene-rich permeate is then transferred into a secondary reaction zone and subjected to a secondary hydroformylation therein with synthesis gas in the presence of an SILP catalyst system. The reaction product obtained from the secondary hydroformylation is recycled into the aldehyde removal stage.

14 Claims, 3 Drawing Sheets

Figure 1:
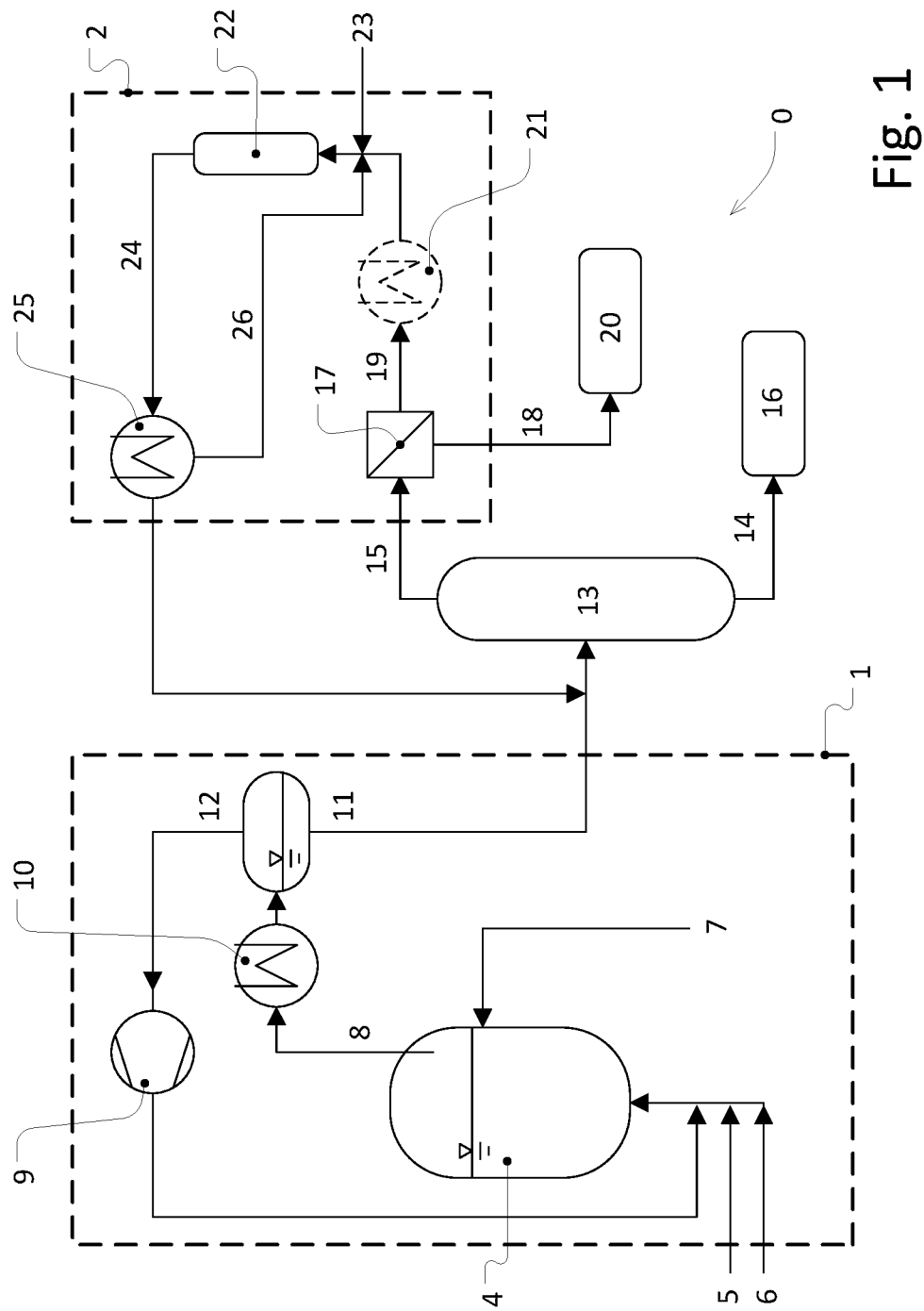

(51) Int. Cl.
(52) U.S. Cl.
CPC ........... *B01D 61/362* (2013.01); *B01D 61/38* (2013.01); *B01J 31/0292* (2013.01); *B01J 31/185* (2013.01); *B01J 31/1845* (2013.01); *B01J 31/24* (2013.01); *C07C 45/786* (2013.01); *C07C 45/79* (2013.01); *C07C 45/82* (2013.01); *B01D 2311/02* (2013.01); *B01D 2311/04* (2013.01); *B01D 2311/06* (2013.01); *B01D 2311/263* (2013.01); *B01D 2311/2669* (2013.01); *B01D 2311/2673* (2013.01); *B01J 2231/321* (2013.01); *B01J 2531/822* (2013.01)

(58) Field of Classification Search
USPC ......................................................... 568/454
See application file for complete search history.

(56) References Cited

U.S. PATENT DOCUMENTS

| | | |
|---|---|---|
| 8,884,070 B2 | 11/2014 | Franke et al. |
| 9,018,420 B2 | 4/2015 | Franke et al. |
| 2016/0068459 A1 | 3/2016 | Dyballa et al. |

FOREIGN PATENT DOCUMENTS

| | | |
|---|---|---|
| WO | 2012/041846 A1 | 4/2012 |
| WO | WO2015/071266 | 5/2015 |
| WO | WO2015/132068 | 9/2015 |

\* cited by examiner

TWO-STAGE HYDROFORMYLATION PROCESS WITH CIRCULATING GAS AND SILP TECHNOLOGY

The invention relates to processes for preparing aldehydes by hydroformylation of alkenes, in which an alkene-containing feed mixture is subjected to a primary hydroformylation with synthesis gas in the presence of a homogeneous catalyst system, the primary hydroformylation being effected in a primary reaction zone from which a cycle gas containing at least some of the products and unconverted reactants of the primary hydroformylation are drawn off continuously and partly condensed, with recycling of uncondensed components of the cycle gas into the primary reaction zone, and with distillative separation of condensed components of the cycle gas in an aldehyde removal stage to give an aldehyde-rich mixture and a low-aldehyde mixture.

The invention further relates to plants and plant complexes and to the use thereof for performing these processes.

In organic chemistry, substance groups are generally classified by the number of carbon atoms therein. The substance class of interest is preceded by the prefix $C_n$ where n is the number of carbon atoms present in the substance. When reference is made to $C_4$ alkenes for example, this is understood to mean the four isomeric olefins having four carbon atoms, namely isobutene, 1-butene, cis-2-butene and trans-2-butene. By contrast, there is only one alkene having three carbon atoms, namely propene, and one $C_3$ alkane, namely propane.

The saturated alkanes have barely any reactivity and are therefore used predominantly as fuel or aerosol propellant.

Meanwhile, it is possible to use the more reactive alkenes to form hydrocarbons having a greater number of carbon atoms which open up a broad spectrum of application and hence achieve higher sale prices than the starting materials having a smaller number of carbon atoms. This is how industrial organic chemistry creates value.

An economically important substance class which is prepared from lower alkenes for this reason is that of the aldehydes.

The aldehydes having four carbon atoms include the isomeric substances n-butanal and isobutanal. They are in global demand in high volumes for the production of vulcanization accelerators, synthetic resins and plasticizers. $C_4$ aldehydes are prepared industrially by $C_3$ hydroformylation.

Hydroformylation (the oxo process) is generally understood to mean the conversion of unsaturated compounds such as olefins (alkenes) in particular with synthesis gas (hydrogen and carbon monoxide) to aldehydes having a number of carbon atoms one higher than the number of carbon atoms in the starting compounds. $C_4$ aldehydes are accordingly prepared by hydroformylating propene.

A good overview of the state of hydroformylation of olefins can be found in

B. Cornils, W. A. Herrmann, "Applied Homogeneous Catalysis with Organometallic Compounds", Vol. 1 & 2, VCH, Weinheim, N.Y., 1996 and in R. Franke, D. Selent, A. Börner, "Applied Hydroformylation", Chem. Rev., 2012, DOI:10.1021/cr3001803.

The aldehydes having five carbon atoms ($C_5$ aldehydes for short) include n-pentanal (valeraldehyde), isopentanal (isovaleraldehyde), sec-pentanal (2-methylbutanal) and tert-pentanal (pivalaldehyde). $C_5$ aldehydes are prepared on the industrial scale by hydroformylation of $C_4$ alkenes.

Pentanals serve, inter alia, as starting materials for obtaining pentanols, pentanoic acids and pentylamines. Decanols, which are intermediates in the production of plasticizers, detergents and lubricants, can be obtained from said aldehydes by aldol condensation and total hydrogenation of the aldol condensate. A corresponding process is described in DE102009001594A1.

Since both butanal and pentanal are important industrial chemicals, there is a large number of oxo process plants worldwide, in which either a $C_3$ or a $C_4$ hydroformylation for preparation of butanal or pentanal is being conducted.

The propene or butene utilized for this purpose is generally obtained in refining or cracking of mineral oil. It is generally the case that the alkenes are in no way available as pure materials, but are always accompanied by further hydrocarbons from other substance classes and also those having more or fewer carbon atoms. For instance, the raw material used for propene hydroformylation is what is called a $C_3$ mixture which, as well as the unsaturated $C_3$ olefin, also contains the saturated $C_3$ alkane propane. More complex mixtures are those called $C_4$ mixtures which are utilized for pentanal preparation: they contain, in varying composition, the different butene isomers and butanes.

Because of the progressive scarcity of mineral oil, alternative sources for $C_3$ and $C_4$ alkenes are increasingly being developed, for instance shale oil or shale gas. Giving details would be beyond the scope of this document; what is important is merely to emphasize that the raw material sources for existing $C_3$ and $C_4$ oxo process plants are changing and, consequently, the existing plants have to be operated with altered feed mixtures. The adjustment of the plants is not trivial, since the product quality of the aldehydes depends to a crucial degree on the composition of the feed mixtures.

The invention essentially addresses the question of how the economic viability of legacy oxo processes can be maintained by technical measures when the quality of the feed mixtures has deteriorated.

More specifically, the invention is concerned with the retrofitting of oxo process plants which work by the "gas recycle process".

In a gas recycle process (or stripping reactor process), the products of the hydroformylation are discharged from the reactor in gaseous form together with excess synthesis gas. A general outline of hydroformylation in a gas recycle process can be found in:

Van Leeuwen, Piet W. N. M. and Claver, Carmen (edit.): Rhodium Catalyzed Hydroformylation. Catalysis by Metal Complexes. Volume 22. Kluwer, 2000, pages 212 ff.

The advantage of an oxo process plant that works by the gas recycle process is its simple apparatus construction. Consequently, $C_3$ hydroformylation is generally accomplished using gas recycle plants.

However, gas recycle plants are much less common in $C_4$ hydroformylation: because of the comparatively low volatility of the $C_5$ aldehydes and especially of the high boilers formed in side reactions, gas recycle processes are regarded as unacceptable for pentanal preparation; cf. van Leeuwen, loc. cit.

Nevertheless, there have been attempts to prepare $C_5$ aldehydes from $C_4$ olefin mixtures in a gas recycle process:

Thus, EP0016285B2 describes a gas recycle process for preparation of valeraldehyde from a $C_4$ mixture containing 2.23% n-butane, 1.06% isobutane, 69.88% 1-butene, 10.06% cis-2-butene and 15.1% trans-2-butene.

Another process for $C_4$ hydroformylation of the type specified at the outset is known from EP2280920B1. The inventors proceed from this closest prior art.

In the gas recycle hydroformylation practised in EP2280920B1 for preparation of valeraldehyde, a starting mixture containing 35% 2-butenes and only 1% 1-butene is used. The remainder is inert butane. The mixture, which is extremely low in 1-butene, is hydroformylated with the aid of a symmetric bisphosphite ligand which is stabilized through addition of a sterically hindered secondary amine. Isononyl benzoate is mentioned as a solvent. With this catalyst system, butene conversions of 60% to 75% are achieved. The aim is to increase these modest conversion values.

One way of increasing the conversion is to recycle the unconverted olefins into the hydroformylation reactor. In this context, however, it should be ensured that inert components such as alkanes or reaction by-products are not additionally recycled into the reactor, since the space-time yield of the process is lowered further in this way. In addition, the cycle gas compressor has to provide a greater power to compress the inert components, which increases the energy demand of the process.

One way of increasing the conversion of the gas recycle process without worsening its efficiency is to purify the unconverted substrate to free it of unhydroformylatable substances before recycling it into the reactor. For instance, DE10128325A1 describes a homogeneously catalysed $C_3$ hydroformylation in the gas recycle process, in which a permeate obtained from the gas discharge with the aid of a membrane separation unit is enriched with the olefins unconverted in the first reactor pass. The permeate is recycled into the gas recycle reactor and subjected again to the hydroformylation therein, in the presence of the rhodium phosphite system already used in the first pass. Inert substances are discharged from the gas recycle process via the retentate of the membrane separation unit, and so the efficiency is enhanced.

Suitable membranes for separation of hydroformylatable alkenes from inert alkanes are known. For instance, U.S. Pat. No. 5,062,866 describes a membrane having high butane/butene separating action which could be of good service in the $C_4$ hydroformylation. Even better suited to olefin removal are those membranes infiltrated with a "carrier", which are capable of entering into compounds with the alkenes, said compounds penetrating through the separation-active membrane material more quickly than the alkanes, which do not enter into any compounds with the carrier. Carriers used are copper ions or silver ions. Such a membrane suitable for long-term operation is described in WO2012167362A1.

With the aid of the alkene/alkane separation-active membranes, it is possible to construct a gas recycle process as described in DE10128325A1, which is capable of achieving higher conversions than a membraneless gas recycle process such as that known from EP2280920B1.

Nevertheless, the conversion of such an arrangement is subject by definition to further limits: For instance, in a gas recycle process with permeate recycling into the reactor, hydroformylation is effected in several passes, but always in the presence of the same catalyst system. The performance of the homogeneous catalyst system in the gas recycle reactor thus ultimately determines the conversion of the overall process.

Another way of enhancing the conversion is to provide for a multistage hydroformylation. In a multistage process, a reaction is executed a number of times in succession, but under different reaction conditions in each stage. Thus, there exist two-stage hydroformylation processes in which, in the first stage, a primary hydroformylation is conducted in the presence of a cobalt catalyst and in which, in a downstream second stage, the olefins unconverted in the first stage are subjected to a secondary hydroformylation in the presence of a rhodium system. The multitude of stages enables combination of the advantages of the respective catalyst systems. For instance, the secondary catalyst system can still be used to convert the constituents of the feed which cannot attack the catalyst system for the primary hydroformylation.

The stages may differ not just in terms of the respective catalyst system used but also by apparatus construction: For instance, U.S. Pat. No. 4,593,127A discloses a two-stage hydroformylation wherein the primary hydroformylation is conducted in a gas recycle process and the secondary hydroformylation has a product drawn off in liquid form. Both stages utilize a conventional metal/organophosphorus complex as a homogeneous catalyst system.

Such catalyst systems are the industry standard. However, a fundamental disadvantage of homogeneous catalyst systems is the difficulty of their removal, since the catalyst complex is dissolved in the reaction system.

It is much easier to remove heterogeneous catalysts which, being solids, remain in the reactor virtually automatically. However, simple solid-state catalysts, because of their low activity, are unsuitable for catalysing a hydroformylation at the desired rate.

A compromise is what are called SILP systems.

An SILP (=supported ion liquid phase) system is understood to mean a catalyst system comprising a solid porous support material with an ionic liquid applied to the surface thereof. Dissolved in the ionic liquid in turn is a homogeneous catalyst system, for example a metal/organophosphorus complex. In this way, the homogeneous catalyst is fixed on the solid support via the ionic liquid. This gives an immobilized homogeneous catalyst which can be handled like a heterogeneous catalyst and significantly eases the separation of the catalyst from the reaction mixture. An SILP system thus combines the advantages of an active homogeneous catalyst with those of an easily handled heterogeneous catalyst.

An SILP system suitable for the $C_3$ and $C_4$ hydroformylation is disclosed in WO2012041846A1.

The viability of the SILP-catalysed hydroformylation of propene and butene has been demonstrated by the scientific literature.

For instance, Riisanger et al. show propene hydroformylation over an SILP catalyst comprising the 2,7-bis(SO3Na)-4,5-bis(diphenylphosphino)-9,9-dimethylxanthene ligand in a modified Rh complex (Rh-sulfoxantphos):

Riisager, A.; Fehrmann, R.; Haumann, M.; Gorle, B. S. K. & Wasserscheid, P. Stability and Kinetic Studies of Supported Ionic Liquid Phase Catalysts for Hydroformylation of Propene Industrial & Engineering Chemistry Research, American Chemical Society, 2005, 44, 9853-9859

The fact that the same SILP system is also suitable for 1-butene hydroformylation is shown by Haumann et al.:

Haumann, M.; Dentler, K.; Joni, J.; Riisager, A. & Wasserscheid, P. Continuous Gas-Phase Hydroformylation of 1-Butene using Supported Ionic Liquid Phase (SILP) Catalysts Adv. Synth. Catal., WILEY-VCH Verlag, 2007, 349, 425-431

Haumann, M.; Jakuttis, M.; Werner, S. & Wasserscheid, P. Supported ionic liquid phase (SILP) catalyzed hydroformylation of 1-butene in a gradient-free loop reactor Journal of Catalysis, 2009, 263, 321-327

The problem addressed by the invention is that of developing the process of the type specified at the outset such that it achieves high conversions and affords aldehyde in good product quality even in the case of a deteriorating raw material position. More particularly, a solution is to be found for making legacy oxo process plants capable of utilizing lower-value raw material sources.

This problem is solved by separating the low-aldehyde mixture into a retentate and a permeate by means of a membrane separation unit in such a way that alkenes present in the low-aldehyde mixture become enriched in the permeate, while alkanes present in the low-aldehyde mixture become enriched in the retentate. The alkene-rich permeate is then transferred into a secondary reaction zone and subjected to a secondary hydroformylation therein with synthesis gas in the presence of an SILP catalyst system. The reaction product obtained from the secondary hydroformylation is recycled into the aldehyde removal stage.

The invention therefore provides a process for preparing aldehydes by hydroformylation of alkenes, in which an alkene-containing feed mixture is subjected to a primary hydroformylation with synthesis gas in the presence of a homogeneous catalyst system, the primary hydroformylation being effected in a primary reaction zone from which a cycle gas containing at least some of the products and unconverted reactants of the primary hydroformylation are drawn off continuously and partly condensed, with recycling of uncondensed components of the cycle gas into the primary reaction zone, and with distillative separation of condensed components of the cycle gas in an aldehyde removal stage to give an aldehyde-rich mixture and a low-aldehyde mixture, wherein the low-aldehyde mixture is separated into a retentate and a permeate by means of a membrane separation unit in such a way that alkenes present in the low-aldehyde mixture become enriched in the permeate, while alkanes present in the low-aldehyde mixture become enriched in the retentate, in which the permeate is transferred into a secondary reaction zone and subjected to a secondary hydroformylation therein with synthesis gas in the presence of an SILP catalyst system, with supply of the reaction product obtained from the secondary hydroformylation to the aldehyde removal stage.

The present invention is based on the finding that SILP technology is outstandingly suitable for converting the other alkenes which have not been converted in the gas recycle process in the presence of an organophosphorus-metal complex to aldehyde by way of a secondary hydroformylation. The combination of a conventionally homogeneously catalysed gas recycle stage with a secondary hydroformylation stage over an SILP system is advantageous because the reactants can be fed to an SILP stage in gaseous form. It is therefore possible with a comparatively low level of technical complexity to add the SILP stage on after a gas recycle stage, by simply running a portion of the cycle gas, either before or after partial compensation thereof, into the SILP stage. A basic idea of the invention is therefore to use a portion of the cycle gas as reactant for the SILP stage. Since, within the SILP stage, the secondary hydroformylation is conducted virtually in the gas phase (from a chemical point of view, the hydroformylation in an SILP system also takes place in the liquid phase, namely within the ionic liquid, but the reactant supply and product removal are more of interest from a technical point of view; both are effected in the gas phase in an SILP stage), it is generally possible to dispense with additional measures for evaporation of the feed to the SILP stage, such that a combined cycle gas/SILP process can be operated particularly efficiently.

Moreover, the SILP stage reduces the volume of the cycle gas circulated, since less unconverted alkenes have to be recycled into the gas recycle reactor because of the enhanced conversion. This lowers the energy consumption of the cycle gas compressor. Nowadays, the energy demand cycle gas compressor is responsible for about 25% of the total operating costs of an oxo process plant, and so savings made here are perceptible.

The invention is additionally based on the finding that the reaction output of the SILP stage does not require a dedicated product removal; instead, the reaction product obtained from the secondary hydroformylation can be worked up together with the reaction product of the primary hydroformylation in a common aldehyde removal. This distinctly reduces the apparatus costs.

Incidentally, a particular advantage of the process of the invention is that the membrane separation unit and the SILP reactor are comparatively small apparatuses which can be added in a simple manner onto an existing gas recycle oxo process plant and the aldehyde removal thereof. Thus, it is possible in this way, from a conventional process according to the preamble of claim 1 which is conducted in a legacy oxo process plant, by subsequent addition of the membrane separation unit and the SILP stage, to arrive at a two-stage process of the invention having a higher conversion than the conventional one-stage process. Therefore, it is possible in accordance with the invention to retrofit legacy oxo processes in a simple manner as soon as the raw material supply to the existing plant deteriorates.

The process of the invention can be used either in $C_3$ hydroformylation or in $C_4$ hydroformylation. The reason for this is that standard SILP systems convert both propene and butene to the corresponding aldehydes. For this reason, the feed mixture used for the first stage may either be a $C_3$ mixture containing between 10% and 90% by weight of alkenes having three carbon atoms or a $C_4$ mixture containing between 10% and 90% by weight of alkenes having four carbon atoms. It will be appreciated that it is also possible to use feed mixtures containing both $C_3$ olefins and $C_4$ olefins as hydroformylatable substrate. It is not impossible for the feed mixture to contain further alkenes having fewer than three or more than four carbon atoms. Preference is certainly given to those mixtures that are particularly homogeneous. In operational practice, however, it is more likely that heterogeneous mixtures have to be processed, even of varying composition.

The particular charm of the invention is that secondary SILP hydroformylation is equally suitable for the extensions of $C_3$ processes and for the extension of $C_4$ processes. Executed at a site where both $C_3$ hydroformylation and $C_4$ hydroformylation are practised, this opens up the possibility of retrofitting just a single SILP stage which is assigned either to the $C_3$ oxo process plant or the $C_4$ oxo process plant. In such an arrangement, there is parallel preparation of $C_4$ aldehydes from the $C_3$ mixture and $C_5$ aldehydes from the $C_4$ mixture, with the proviso that the $C_3$ mixture is subjected to a primary $C_3$ hydroformylation with synthesis gas in the presence of a homogeneous catalyst system, the primary $C_3$ hydroformylation being effected in a primary $C_3$ reaction zone from which a $C_3$ cycle gas containing at least some of the products and unconverted reactants of the primary $C_3$ hydroformylation are drawn off continuously and partly condensed, and uncondensed components of the $C_3$ cycle gas being recycled into the primary $C_3$ reaction zone, and the condensed components of the $C_3$ cycle gas being separated by distillation in a $C_4$ aldehyde removal stage to give a $C_4$ aldehyde-rich mixture and a low-$C_4$ aldehyde mixture, and in that the $C_4$ mixture is subjected to a primary $C_4$ hydroformylation with synthesis gas in the presence of a homogeneous catalyst system, the primary $C_4$ hydroformylation being effected in a primary $C_4$ reaction zone from which a $C_4$ cycle gas containing at least some of the products and unconverted reactants of the primary $C_4$ hydroformylation are drawn off continuously and partly condensed, and uncondensed components of the $C_4$ cycle gas being recycled into the primary $C_4$ reaction zone, and the condensed components of the $C_4$ cycle gas being separated by distillation in a $C_5$ aldehyde removal stage to give a $C_5$ aldehyde-rich mixture and a low-$C_5$ aldehyde mixture, wherein, optionally, the low-$C_4$ aldehyde mixture or the low-$C_5$ aldehyde mixture is fed to the membrane separation unit and the resultant permeate is subjected to the secondary hydroformylation in the presence of the SILP catalyst system, and wherein the reaction product obtained from the secondary hydroformylation is fed to the corresponding $C_4$ or $C_5$ aldehyde removal stage.

The advantage of this assignment of the SILP stage either to the $C_3$ plant or to the $C_4$ plant is advantageous especially when both the $C_3$ mixture supplied and the $C_4$ mixture supplied are subject to qualitative variations to different degrees. According to which raw material source is currently delivering the poorer quality, the SILP stage is assigned to the respective oxo process plant utilizing this raw material stream. It will be appreciated that the SILP stage can also be assigned to the oxo process plants having the aldehydes of which greater volumes are being demanded at that time.

In this way, by means of a modest new installation of a membrane removal stage and an SILP stage alongside the two oxo process plants, a considerable increase is obtained in the production and raw material flexibility.

What is crucial to the success of the process of the invention is that, by means of the membrane separation process, the low-aldehyde stream from the aldehyde removal is depleted very substantially of inert components which are not available to the SILP stage as a hydroformylatable substrate. These especially include the alkanes which, because of their virtually identical molecular weight, can barely be separated by distillation from the corresponding olefins. A particularly effective separation of the non-hydroformylatable alkanes can be effected with the aid of a membrane separation unit comprising at least one membrane having a separation-active membrane material, wherein the membrane separation unit has been provided with a carrier medium so capable of entering into compounds with alkenes for which the membrane material has a higher permeability than for the corresponding non-compounded alkenes. The carrier medium is understood to mean a carrier which combines with the alkenes to be enriched in the permeate to give compounds which permeate preferentially through the membrane material. In this way, the separation sharpness of the membrane in the direction of the alkenes is distinctly enhanced. The carrier medium or carrier does not enter into any compound with the less reactive alkenes, and so the alkanes permeate much more slowly and are consequently preferentially enriched in the retentate. Suitable carrier media are especially copper ions or silver ions.

A suitable membrane having high butane/butene separating action is described in U.S. Pat. No. 5,062,866.

Ho et al. describe a "Supported Liquid Membrane" in which the liquid is a silver solution having a high preferential solubility for olefins:

W. S. Ho, D. C. Dalrymple, Facilitated transport of olefins in Ag+-containing polymer membranes, Journal of Membrane Science 91 (1994) 13-25.

Such a membrane is also of good suitability for the purpose intended here. This is all the more true when the supported liquid membrane described by Ho et al. is disposed directly within the vapour stream of the column utilized for aldehyde removal, i.e. still upstream of the top condenser of the column.

This does not necessitate any additional compensation, and the vapour stream which is condensed and applied to the column in liquid form is distinctly reduced because of the removal of the permeate. This saves energy costs through reduction of the return stream. Moreover, the top pressure of the column according to Ho et al. affords a better $C_4$ olefin flow rate through the membrane, with only a very slight decrease in the separation factor of $C_4$ olefins with respect to $C_4$ alkanes. Because of a subsequent hydroformylation in the gas phase in an SILP reactor, the permeate stream need not be compressed to such a high degree as in a conventional liquid phase hydroformylation, and consequently saves additional energy costs compared to the conventional process. The column return stream is then fed from the membrane retentate.

Further suitable membranes with olefin/paraffin separating action are disclosed in R. Faiz, K. Li, Olefin/paraffin separation using membrane based facilitated transport/chemical absorption techniques, Chemical Engineering Science 73 (2012) 261-284.

R. Faiz, K. Li, Polymeric membranes for light olefin/paraffin separation, Desalination 287 (2012) 82-97.

A commercially available membrane or system olefin/paraffin separation by means of membrane processes is supplied by IMTEX Membranes Corp., Mississauga, Canada. IMTEX describes a process for long-term operation of an olefin/paraffin-selective membrane in WO2012/167362A1.

The SILP catalyst system of the secondary hydroformylation preferably comprises the following components:
 a) a solid porous carrier material;
 b) an ionic liquid;
 c) a metal selected from group 9 of the Periodic Table of the Elements;
 d) a phosphorus-containing organic ligand;
 e) optionally an organic amine.

Such an SILP system is described in WO2012041846A1.

Preferably, the permeate from the membrane separation stage enters the secondary reaction zone in gaseous form. This reduces the energy consumption because of lower compressor outputs compared to a conventional liquid phase hydroformylation. This is all the more true when the permeate is obtained in gaseous form in the membrane separation unit. This will be the case when the transmembrane pressure measured across the membrane is so great that permeate virtually evaporates at the membrane because of the pressure drop (gas permeation). In that case, further measures for evaporation of the permeate prior to entry into the SILP stage can be dispensed with.

If the permeate is obtained at least partly in liquid form in the membrane separation unit, however, an evaporator is needed, which fully evaporates the liquid permeate by means of the action of heat prior to entry into the SILP stage. The heat required for the purpose can be obtained, for example, from the condenser which is utilized in the primary hydroformylation for partial compensation of the cycle gas. In this way, energy is saved.

The catalyst system utilized in the gas recycle process is preferably a conventional rhodium/phosphine or phosphite or phosphoramidite system, dissolved fully in the liquid phase of the reaction mixture of the primary reaction zone.

The invention also provides a plant for preparation of aldehydes by hydroformylation of alkenes, comprising a membrane separation unit and a secondary reaction zone disposed in the permeate of the membrane separation unit and with an SILP catalyst system present therein.

This plant comprises the assemblies which have to be added onto a legacy oxo process plant in order to be able to conduct the process of the invention.

Preferably, the membrane separation unit of the plant has a carrier medium/carrier to increase the alkene selectivity and the membrane.

The SILP catalyst system of the plant preferably has the abovementioned features a) to d) and optionally also e).

The invention also provides a plant complex for performance of a process of the invention using the inventive extension of the plant. In that case, such a plant complex is composed of a first complex component for the performance of the primary hydroformylation and of a second complex component in which the secondary hydroformylation is conducted. The first complex component corresponds to the legacy oxo process plant, while the second complex is the inventive extension. The first and second complex components should be connected to one another in such a way that the membrane separation unit of the second complex component can be charged with at least one aldehyde-containing stream from the first complex component.

As already outlined, the inventive extension can be combined with different oxo process plants operated in parallel. In this way, a preferred development of the invention envisages that a plant complex consisting of three complex components is operated, wherein a primary hydroformylation is conducted in the first and third complex components, while the SILP-based hydroformylation is conducted in the second complex component. In that case, the SILP stage can be charged with an aldehyde-containing stream from the first complex component and/or from the third complex component.

If the two secondary hydroformylations produce different aldehydes, they will also have a dedicated aldehyde removal stage set up for the removal of the aldehyde having the appropriate carbon number. What correspondingly follows is the recycling of the reaction product from the secondary reaction zone of the second complex component into the aldehyde removal stage of the first or third complex component, according to which complex component the low-aldehyde stream fed to the secondary hydroformylation comes from: in principle, the reaction output of the SILP stage is recycled into the aldehyde removal stage from which the feed to the SILP stage ultimately comes.

As already explained above, a basic idea of the invention is to use a portion of the cycle gas as reactant for the SILP stage. The portion of the cycle gas which is run as reactant to the SILP stage can be taken from the gas recycle process either before or after the partial condensation.

What have been outlined so far are the embodiments of the invention in which the SILP stage follows after the partial condensation and is effectively fed from the condensed components of the cycle gas.

According to the invention, it is alternatively possible for the second reaction zone to precede the partial condensation and for it to be fed directly with cycle gas drawn off from the first reaction zone. The effluent of the SILP stage is then fed to the partial condensation, such that the SILP discharge is ultimately worked up by means of the same column which also takes care of the aldehyde removal in the gas recycle stage.

The invention therefore also provides a process for preparing aldehydes by hydroformylation of alkenes, in which an alkene-containing feed mixture is subjected to a primary hydroformylation with synthesis gas in the presence of a homogeneous catalyst system, the primary hydroformylation being effected in a primary reaction zone from which a cycle gas containing at least some of the products and unconverted reactants of the primary hydroformylation are drawn off continuously and partly condensed, with recycling of uncondensed components of the cycle gas into the primary reaction zone, and with distillative separation of condensed components of the cycle gas in an aldehyde removal stage to give an aldehyde-rich mixture and a low-aldehyde mixture, in which the cycle gas, prior to the partial condensation thereof, is separated into a retentate and a permeate by means of a membrane separation unit, wherein alkenes present in the cycle gas become enriched in the permeate, while alkanes present in the cycle gas become enriched in the retentate, and wherein the permeate is transferred into a secondary reaction zone and subjected to a secondary hydroformylation therein with synthesis gas in the presence of an SILP catalyst system, and wherein the reaction product obtained from the secondary hydroformylation is supplied to the partial condensation.

As in the other arrangement variant of the membrane separation unit, in the case of charging of the membrane separation unit with as yet uncondensed cycle gas too, a membrane separation unit having a separation-active membrane material which has been provided with a carrier medium capable of entering into compounds with alkenes for which the membrane material has a higher permeability than for the corresponding non-compounded alkenes is used.

In this variant too, the SILP system of the second hydroformylation stage comprises the above-discussed components a) to d) and optionally also e).

In the catalyst system in the primary hydroformylation (gas recycle stage), preference is given to using a conventional homogeneous catalyst system comprising rhodium and at least one phosphine or phosphite or phosphoramidite ligand, the homogeneous catalyst system being fully dissolved in a liquid phase of the reaction mixture of the primary reaction zone.

The particular advantage of the retrofit described here, comprising essentially the membrane separation unit and the SILP stage, is that it can equally be arranged upstream or downstream of the partial condensation of the cycle gas.

The present invention therefore also provides a plant complex for the performance of a process, in which the SILP stage precedes the partial compensation, using the universally usable retrofit, such that the plant complex has a first complex component for the performance of a primary hydroformylation and a second complex component for the performance of a secondary hydroformylation, it being possible to charge the membrane separation unit of the second complex component with the cycle gas from the first complex component.

Since the particular advantages of the invention are achieved especially by way of retrofitting an existing plant, the invention likewise provides for the use of a plant comprising membrane separation and SILP hydroformylation for retrofitting of an existing plant for homogeneously catalysed hydroformylation which especially works by the gas recycle process.

It will be appreciated that it is also possible to design an inventive oxo process plant that works in two stages as a complete new plant.

Figure 2:
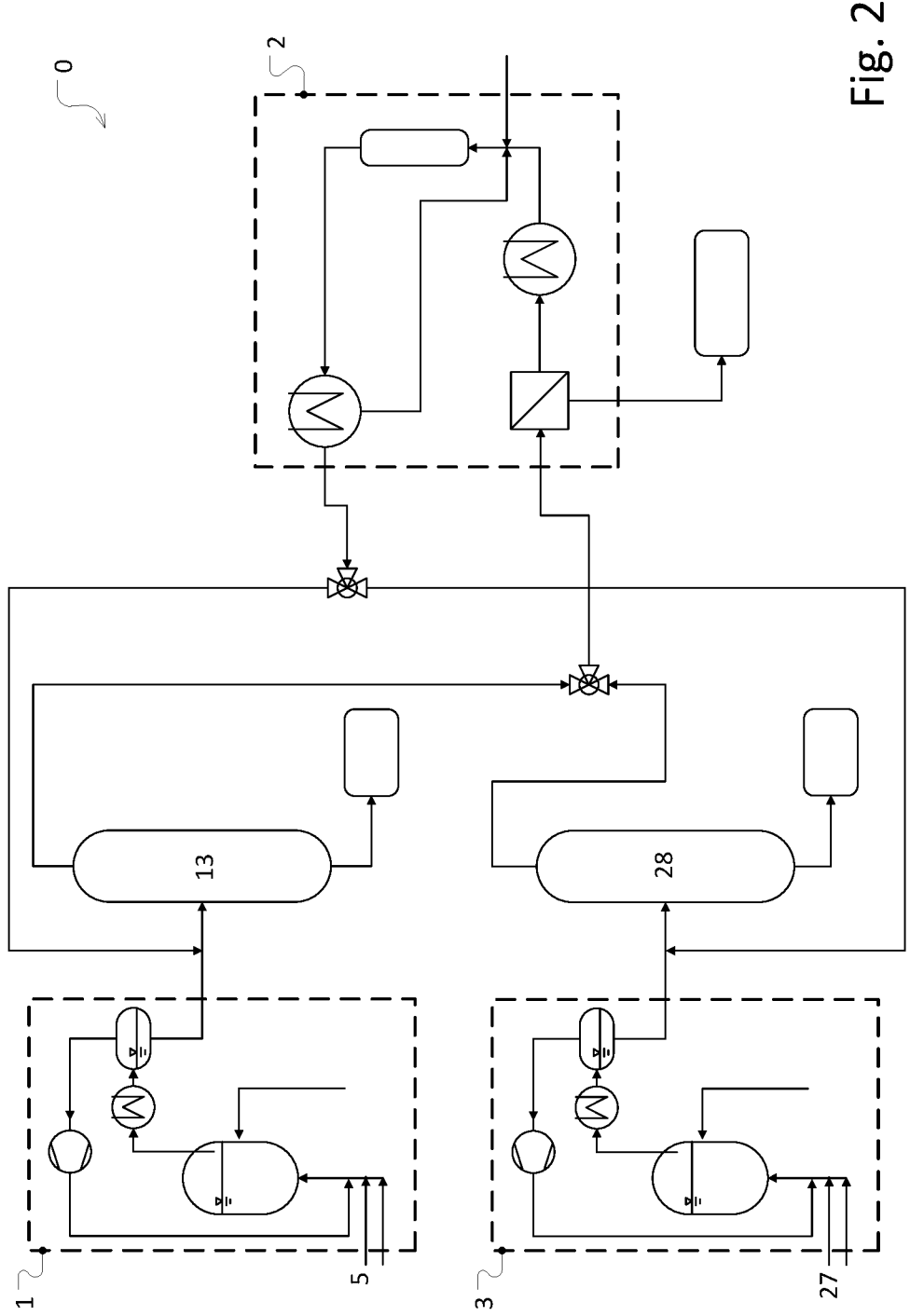
Figure 3:
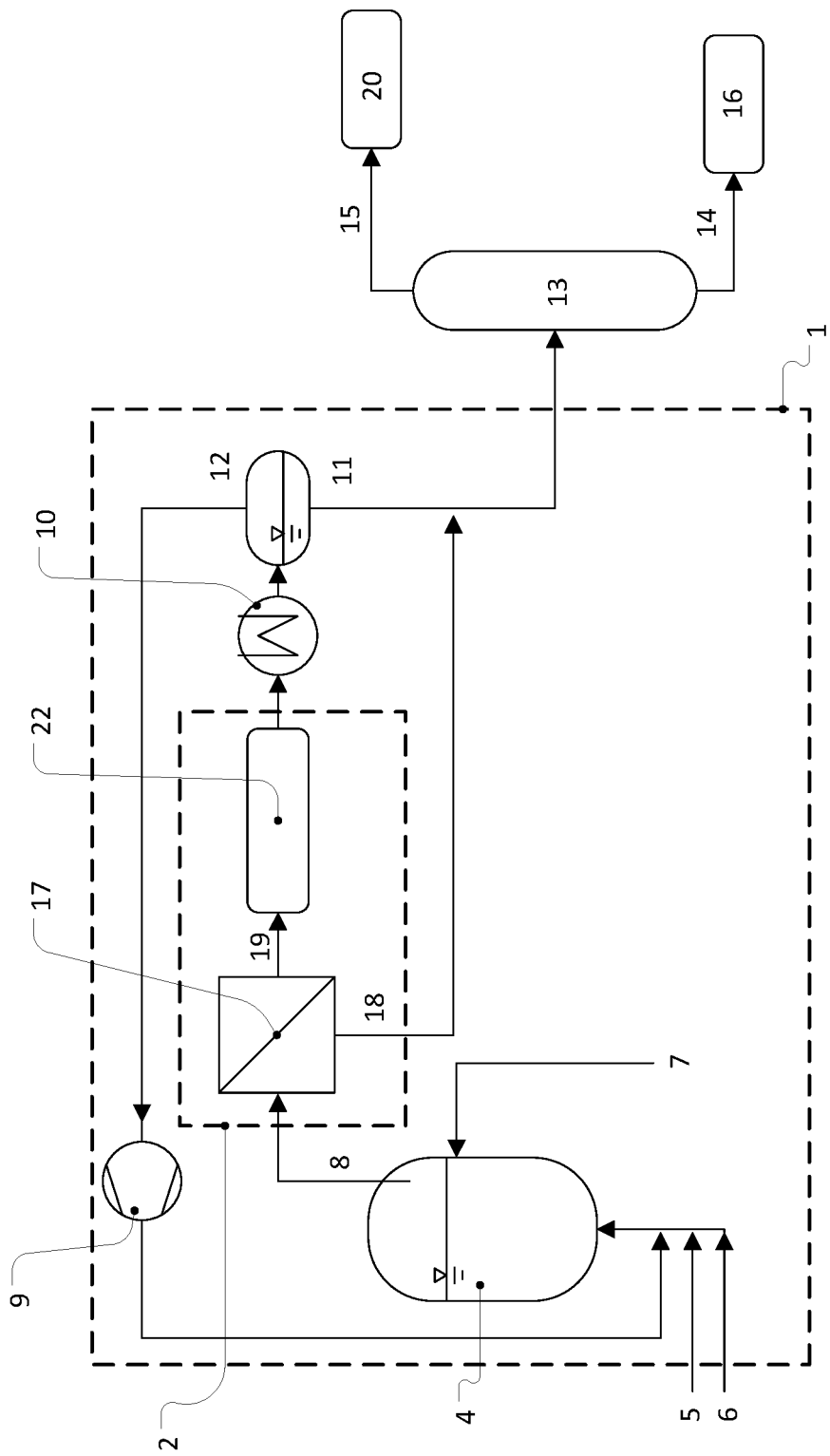

The invention is now to be elucidated by working examples. The figures show:

FIG. 1: a simplified process flow diagram of a two-stage oxo process according to the invention, in which the SILP stage follows after the partial condensation of the cycle gas;

FIG. 2: a simplified process flow diagram of a plant complex having two primary hydroformylations;

FIG. 3: a simplified process flow diagram of a two-stage oxo process according to the invention, in which the SILP stage precedes the partial condensation of the cycle gas.

FIG. 1 shows a simplified process flow diagram for performance of a two-stage hydroformylation. The plant complex 0 necessary for the process is composed of a first complex component 1 and a second complex component 2. The first complex component 1 serves for conduction of a primary hydroformylation, for example of butenes, in the gas recycle method, while the second complex component 2 is intended for the conversion of the butenes unconverted in the first complex component 1 by way of a secondary SILP hydroformylation.

The first complex component 1 corresponds to a conventional gas recycle plant for butene hydroformylation, as known, for example, from EP2280920B1.

At the core of the gas recycle plant is a primary reaction zone 4, for example in the form of a bubble column reactor of a stirred tank, a loop reactor or a jet nozzle reactor. Within the primary reaction zone 4, a liquid reaction phase and a gaseous reaction phase are formed. The liquid phase is formed essentially from liquid reaction product ($C_5$ aldehyde), dissolved synthesis gas and butenes, and also from dissolved homogeneous catalyst. In addition, liquid solvents, for example isononyl benzoate, may be present.

A $C_4$ mixture 5 which comprises butenes and is to be hydroformylated and synthesis gas 6 consisting of carbon monoxide and hydrogen are run into the primary reaction zone 4. If required, fresh catalyst 7 is likewise run into the primary reaction zone 4. The catalyst 7 is especially a conventional rhodium/phosphite system.

In a manner known per se, within the primary reaction zone 4, the $C_4$ mixture 5 is reacted with synthesis gas 6 in the presence of the homogeneously dissolved catalyst 7 to give corresponding $C_5$ aldehydes. The $C_5$ aldehydes are drawn off as cycle gas 8 from the gas phase of the primary reaction zone 4 together with excess synthesis gas. The cycle gas 8 is sucked out by means of a cycle gas compressor 9. A heat exchanger-condenser combination 10 partly condenses the cycle gas 8. This affords a condensate 11 comprising essentially the $C_5$ aldehydes, and also unconverted butenes and inert constituents of the $C_4$ mixture 5. The uncondensed constituents of the cycle gas 12 comprise essentially unconverted synthesis gas. They are returned to the primary reaction zone 4, i.e. the cycle gas reactor.

Meanwhile, the condensate 11 is transferred to an aldehyde removal stage 13. The aldehyde removal stage 13 works essentially by distillation. Thus, the condensate 11 is separated into an aldehyde-rich mixture 14 and a low-aldehyde mixture 15.

The aldehyde-rich mixture 14 is guided to an aldolization 16, in order to be subjected therein to an aldol condensation in a manner known per se. This process is described in DE102009001594A1.

Meanwhile, the low-aldehyde mixture 15, preferably the uncondensed vapour from the distillation column utilized as aldehyde removal stage, is transferred into the second complex component 2. It is first fed therein to a membrane separation unit 17 and separated therein into a retentate 18 and a permeate 19. The membrane separation unit 17 may, in a manner known per se, comprise one or more membrane modules connected to one another in parallel or series. The exact configuration of the membrane separation unit is not what matters here. What is instead crucial is that the membrane separation unit 17 is suitable for enriching the olefins present in the low-aldehyde mixture 15 in its permeate 19, while the inert alkanes become enriched in the retentate 18. Suitable membranes are described in the prior art cited above.

The butanes present in the low-aldehyde mixture 15 originally come from the $C_4$ mixture 5 and are additionally formed in a hydrogenating side reaction within the primary reaction zone 4 from butenes and hydrogen. The butanes are no longer directly amenable to the hydroformylation, and so they are discharged via the retentate 18 of the membrane separation unit and sent to a butane utilization 20. The butane utilization 20 which is not described in detail here comprises essentially a hydrogenation of the unsaturated compounds remaining and a purification. The butane thus obtained can be utilized as motor fuel or as heating fuel.

Should the membrane separation unit 17 be fed directly from the vapour of the aldehyde removal stage 13, a portion of the retentate is fed to the top condenser (not shown) of the distillation column utilized as the aldehyde removal stage. The portion of the retentate branched off then corresponds to the column return stream.

The alkenes not hydroformylated within the primary reaction zone 4 in the first pass ultimately accumulate in the permeate 19 of the membrane separation unit 17. If the transmembrane pressure is high enough, the permeate virtually evaporates on exit from the membrane. Should the permeate 19 not yet have evaporated completely, it can be evaporated by means of an optional evaporator 21. The evaporator 21 is operated with heat from the heat exchanger 10 in order to save energy. Beyond the evaporator 21 or earlier, the permeate 19 is gaseous. In this state, it is transferred into a secondary reaction zone 22 and subjected to a secondary hydroformylation therein over an SILP catalyst system. The secondary hydroformylation also requires synthesis gas. If this is not present to a sufficient degree in the permeate 19, additional synthesis gas 23 is metered in. The secondary hydroformylation in the secondary reaction zone 22 is effected in the presence of an SILP catalyst system in a manner known per se as described in WO2012041846A1. The reaction output 24 from the secondary reaction zone 22 is likewise gaseous. It is cooled in a cooler 25, and is partly liquefied again. Synthesis gas 26 which outgases in the process can be recycled into the secondary reaction zone 22. The cooled reaction output 24 from the secondary hydroformylation is finally conducted back into the aldehyde removal stage 13. The $C_5$ aldehydes formed in the SILP hydroformylation are therefore removed in the same aldehyde removal stage 13 as the pentanals which are formed in the primary hydroformylation in the first complex component 1. The second stage in the second complex component 2 thus does not need any dedicated aldehyde removal stage.

In a preferred development of the invention, the second complex component 2 comprising essentially the membrane separation unit 17 and the secondary reaction zone 22 is an extension of an existing gas recycle plant 1.

A particular advantage can be achieved by the invention when a $C_4$ hydroformylation 1 is being operated alongside a $C_3$ hydroformylation 3 within an integrated site. In a preferred development of the invention, it is possible to supplement the $C_3$ oxo process plant 3 and the $C_4$ oxo process plant 1 with an SILP hydroformylation 2 which can optionally be combined with the C4 oxo process plant 1 and the C3 oxo process plant 3. In this way, the plant complex 0 shown in FIG. 2 comprising three complex components 1, 2, 3 is obtained.

Depending on the product quality of the $C_4$ mixture 5 used for the first complex component and the $C_3$ mixture 27 used for the third complex component 3, the SILP complex 2 is coupled either to the $C_4$ oxo process plant 1 or to the $C_3$ oxo process plant 3. In that case, the recycling from the SILP process is effected into the $C_5$ aldehyde removal stage 13 or the $C_4$ aldehyde removal stage 28.

In this way, the three-part plant complex from FIG. 2 can be used to react to different product qualities of the mixtures 5, 27 provided or the particular demand for butanal or pentanal.

FIG. 3 shows a further embodiment of the invention in which the second complex component 2 is arranged within the first complex component 1, namely upstream of the heat exchanger/condenser combination 10 in which the partial condensation of the cycle gas 8 is effected. The membrane separation unit 17 is charged directly with the cycle gas 8 drawn off fresh from the primary hydroformylation. Alkenes present in the cycle gas 8 become enriched in the permeate 19 of the membrane separation unit 17 and are fed to the SILP-based secondary reaction zone 22 in order to be converted therein. The non-hydroformylatable alkanes collect preferentially in the retentate 18 of the membrane separation unit 17 and are discharged from the cycle gas in the direction of the aldehyde removal stage 13. This reduces the burden on the cycle gas compressor 9.

The reaction output 24 from the secondary hydroformylation 22 is fed to the heat exchanger/condenser combination 10, such that the workup of the output from the two hydroformylations 4, 22 is effected together in the aldehyde removal stage 13.

The advantage of this configuration of the invention over the variant shown in FIG. 1 is that it is possible to dispense with up to two heat exchangers. The disadvantage is the greater volume flow rate through the SILP stage, such that the dimensions of the membrane separation unit 17 and the secondary reaction zone 22 have to be increased correspondingly. The ultimate decision is made via a consideration of economic viability in relation to the preferred process variant.

LIST OF REFERENCE SYMBOLS 0 plant complex
1 first complex component ($C_4$ oxo process plant)
2 second complex component (SILP plant)
3 third complex component ($C_3$ oxo process plant)
4 primary reaction zone
5 $C_4$ mixture
6 synthesis gas
7 catalyst
8 cycle gas
9 cycle gas compressor
10 heat exchanger/condenser combination
11 condensate
12 uncondensed constituents of the cycle gas
13 ($C_5$) aldehyde removal stage
14 aldehyde-rich mixture
15 low-aldehyde mixture
16 aldol condensation
17 membrane separation unit
18 retentate
19 permeate
20 butane utilization
21 evaporator
22 secondary reaction zone
23 additional synthesis gas
24 reaction output from the secondary hydroformylation
25 cooler
26 outgassing synthesis gas
27 $C_3$ mixture
28 $C_4$ aldehyde removal stage

What is claimed is:

1. Process for preparing aldehydes by hydroformylation of alkenes, in which an alkene-containing feed mixture is subjected to a primary hydroformylation with synthesis gas in the presence of a homogeneous catalyst system, the primary hydroformylation being effected in a primary reaction zone from which a cycle gas containing at least some of the products and unconverted reactants of the primary hydroformylation are drawn off continuously and partly condensed, with recycling of uncondensed components of the cycle gas into the primary reaction zone, and with distillative separation of condensed components of the cycle gas in an aldehyde removal stage to give an aldehyde-rich mixture and a low-aldehyde mixture, wherein the low-aldehyde mixture is separated into a retentate and a permeate by means of a membrane separation unit in such a way that alkenes present in the low-aldehyde mixture become enriched in the permeate, while alkanes present in the low-aldehyde mixture become enriched in the retentate, and in that the permeate is transferred into a secondary reaction zone and subjected to a secondary hydroformylation therein with synthesis gas in the presence of an SILP catalyst system, with supply of the reaction product obtained from the secondary hydroformylation to the aldehyde removal stage.

2. Process according to claim 1, wherein the feed mixture used is a $C_3$ mixture containing between 10% and 90% by weight of alkenes having three carbon atoms, based on the total weight of the feed mixture.

3. Process according to claim 1, wherein the feed mixture used is a $C_4$ mixture containing between 10% and 90% by weight of alkenes having four carbon atoms, based on the total weight of the feed mixture.

4. Process according to claim 1, mixture and a second feed mixture are used, whereby the first feed mixture used is a $C_3$ mixture containing between 10% and 90% by weight of alkenes having three carbon atoms, based on the total weight of the first feed mixture, whereby the second feed mixture used is a $C_4$ mixture containing between 10% and 90% by weight of alkenes having four carbon atoms, based on the total weight of the second feed mixture, whereby is parallel preparation of $C_4$ aldehydes from the $C_3$ mixture and $C_5$ aldehydes from the $C_4$ mixture, with the proviso that the $C_3$ mixture is subjected to a primary $C_3$ hydroformylation with synthesis gas in the presence of a homogeneous catalyst system, the primary $C_3$ hydroformylation being effected in a primary $C_3$ reaction zone from which a $C_3$ cycle gas containing at least some of the products and unconverted reactants of the primary $C_3$ hydroformylation are drawn off continuously and partly condensed, and uncondensed components of the $C_3$ cycle gas being recycled into the primary $C_3$ reaction zone, and the condensed components of the $C_3$ cycle gas being separated by distillation in a $C_4$ aldehyde removal stage to give a $C_4$ aldehyde-rich mixture and a low-$C_4$ aldehyde mixture, and in that the $C_4$ mixture is subjected to a primary $C_4$ hydroformylation with synthesis gas in the presence of a homogeneous catalyst system, the primary $C_4$ hydroformylation being effected in a primary $C_4$ reaction zone from which a $C_4$ cycle gas containing at least some of the products and unconverted reactants of the primary $C_4$ hydroformylation are drawn off continuously and partly condensed, and uncondensed components of the $C_4$ cycle gas being recycled into the primary $C_4$ reaction zone, and the condensed components of the $C_4$ cycle gas being separated by distillation in a $C_5$ aldehyde removal stage to give a $C_5$ aldehyde-rich mixture and a low-$C_5$ aldehyde mixture, wherein, optionally, the low-$C_4$ aldehyde mixture or the low-$C_5$ aldehyde mixture is fed to the membrane separation unit and the resultant permeate is subjected to the secondary hydroformylation in the presence of the SILP catalyst system, and wherein the reaction product obtained from the secondary hydroformylation is fed to the corresponding $C_4$ or $C_5$ aldehyde removal stage.

5. Process according to claim 1, wherein the membrane separation unit comprises at least one membrane having a separation-active membrane material, whereby the membrane separation unit has been provided with a carrier medium capable of entering into compounds with alkenes for which the membrane material has a higher permeability than for the corresponding non-compounded alkenes.

6. Process according to claim 1, wherein the SILP catalyst system of the secondary hydroformylation comprises the following components:
   a) a solid porous carrier material;
   b) an ionic liquid;
   c) a metal selected from group 9 of the Periodic Table of the Elements;
   d) a phosphorus-containing organic ligand;
   e) optionally an organic amine.

7. Process according to any of claim 1, wherein the permeate enters the secondary reaction zone in gaseous form.

8. Process according to claim 7, wherein the permeate is obtained at least partly in liquid form in the membrane separation unit and, prior to entry into the secondary reaction stage, is evaporated by the action of heat by means of an evaporator.

9. Process according to claim 7, wherein the permeate is obtained in gaseous form in the membrane separation unit.

10. Process according to claim 1, wherein the homogeneous catalyst system of the primary hydroformylation comprises rhodium and at least one phosphine or phosphite or phosphoramidite ligand, the homogeneous catalyst system being fully dissolved in a liquid phase of the reaction mixture of the primary reaction zone.

11. Process for preparing aldehydes by hydroformylation of alkenes, in which an alkene-containing feed mixture is subjected to a primary hydroformylation with synthesis gas in the presence of a homogeneous catalyst system, the primary hydroformylation being effected in a primary reaction zone from which a cycle gas containing at least some of the products and unconverted reactants of the primary hydroformylation are drawn off continuously and partly condensed, with recycling of uncondensed components of the cycle gas into the primary reaction zone, and with distillative separation of condensed components of the cycle gas in an aldehyde removal stage to give an aldehyde-rich mixture and a low-aldehyde mixture, wherein the cycle gas, prior to the partial condensation thereof, is separated into a retentate and a permeate by means of a membrane separation unit in such a way that alkenes present in the cycle gas become enriched in the permeate, while alkanes present in the cycle gas become enriched in the retentate, and in that the permeate is transferred into a secondary reaction zone and subjected to a secondary hydroformylation therein with synthesis gas in the presence of an SILP catalyst system, with supply of the reaction product obtained from the secondary hydroformylation to the partial condensation stage.

12. Process according to claim 11, wherein the membrane separation unit comprises at least one membrane having a separation-active membrane material, wherein the membrane separation unit has been provided with a carrier medium capable of entering into compounds with alkenes for which the membrane material has a higher permeability than for the corresponding non-compounded alkenes.

13. Process according to claim 11, wherein the SILP catalyst system of the secondary hydroformylation comprises the following components:
   a) a solid porous carrier material;
   b) an ionic liquid;
   c) a metal selected from group 9 of the Periodic Table of the Elements;
   d) a phosphorus-containing organic ligand;
   e) optionally an organic amine.

14. Process according to claim 11, wherein the homogeneous catalyst system of the primary hydroformylation comprises rhodium and at least one phosphine or phosphite or phosphoramidite ligand, the homogeneous catalyst system being fully dissolved in a liquid phase of the reaction mixture of the primary reaction zone.

* * * * *

UNITED STATES PATENT AND TRADEMARK OFFICE
CERTIFICATE OF CORRECTION

| | | |
|---|---|---|
| PATENT NO. | : 9,624,153 B2 | Page 1 of 1 |
| APPLICATION NO. | : 15/103842 | |
| DATED | : April 18, 2017 | |
| INVENTOR(S) | : Marc Becker et al. | |

It is certified that error appears in the above-identified patent and that said Letters Patent is hereby corrected as shown below:

In the Claims

Column 14, Line 46, Claim 4:   After the phrase "Process according to claim 1," insert the phrase --wherein a first feed--

Column 15, Line 36, Claim 7:   After the phrase "Process according to" delete the phrase "any of"

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*